(12) United States Patent
Nakayama

(10) Patent No.: US 10,603,011 B2
(45) Date of Patent: Mar. 31, 2020

(54) ULTRASOUND PROBE AND CORRECTION METHOD FOR THE ULTRASOUND PROBE

(71) Applicant: Konica Minolta, Inc., Tokyo (JP)

(72) Inventor: Yuta Nakayama, Ichikawa (JP)

(73) Assignee: KONICA MINOLTA, INC., Toyota (JP)

( * ) Notice: Subject to any disclaimer, the term of this patent is extended or adjusted under 35 U.S.C. 154(b) by 333 days.

(21) Appl. No.: 15/695,662

(22) Filed: Sep. 5, 2017

(65) Prior Publication Data

US 2018/0078238 A1 Mar. 22, 2018

(30) Foreign Application Priority Data

Sep. 16, 2016 (JP) .................. 2016-181717

(51) Int. Cl.
*A61B 8/00* (2006.01)
*B06B 1/06* (2006.01)
*B06B 1/02* (2006.01)

(52) U.S. Cl.
CPC .......... *A61B 8/4477* (2013.01); *A61B 8/4483* (2013.01); *B06B 1/0215* (2013.01); *B06B 1/0603* (2013.01); *B06B 1/0607* (2013.01); *B06B 1/0622* (2013.01); *A61B 8/4281* (2013.01); *A61B 8/4405* (2013.01)

(58) Field of Classification Search
CPC ... A61B 8/4281; A61B 8/4405; A61B 8/4477; A61B 8/4483; B06B 1/0215; B06B 1/0603; B06B 1/0607; B06B 1/0622
See application file for complete search history.

(56) References Cited

PUBLICATIONS

C. Wang, et al; A micromachined Piezoelectric Ultrasonic Transducer Operating in d33 Mode Using Square Interdigital Electrodes; IEEE Sensors Journal, vol. 7, No. 7, Jul. 2007; pp. 967-976.

*Primary Examiner* — Amelie R Davis
*Assistant Examiner* — Alexei Bykhovski
(74) *Attorney, Agent, or Firm* — Lucas & Mercanti, LLP

(57) ABSTRACT

An ultrasound probe includes: a plurality of ultrasound transducers each including a diaphragm, a lower electrode laminated on a surface of the diaphragm, a piezoelectric film laminated on a surface of the lower electrode, and including an effective area in which larger vibration is caused upon piezoelectric conversion, and a reference area in which smaller vibration than that in the effective area is caused upon piezoelectric conversion, and an upper electrode laminated on a surface of the piezoelectric film; and hardware processors that correct variation in performance between the ultrasound transducers, wherein one or both of the lower electrode and the upper electrode include an effective area electrode portion, and a reference area electrode portion, and each of the hardware processors is a device that corrects one or both of an output value from the effective area electrode portion and an input value to the effective area electrode portion.

18 Claims, 4 Drawing Sheets

ULTRASOUND PROBE AND CORRECTION METHOD FOR THE ULTRASOUND PROBE

Japanese Patent Application No. 2016-181717 filed on Sep. 16, 2016, including description, claims, drawings, and abstract the entire disclosure is incorporated herein by reference in its entirety.

BACKGROUND

Technological Field

The present invention relates to an ultrasound probe and a correction method for the ultrasound probe.

Description of the Related Art

An ultrasound diagnosis apparatus transmits an ultrasound pulse from an ultrasound probe into a subject, receives an echo signal from inside the subject with the ultrasound probe, and converts the echo signal into an electric signal. The ultrasound probe has an ultrasound transducer that converts an electric signal into a mechanical vibration or converts a mechanical vibration into an electric signal. Conventional ultrasound diagnosis apparatuses mainly use thickness vibration of a piezoelectric material used for ultrasound probes, so that the piezoelectric material have a thickness of about ¼ of a wavelength, that is, about 100 μm.

In recent years, ultrasound transducers which are miniaturized for high density arrangement using semiconductor microfabrication technologies (MEMS technologies) have been proposed (e.g., see Chao Wang, Zheyao Wang, Tian-Ling Ren, Senior Member, IEEE, Yiping Zhu, Yi Yang, Xiaoming Wu, Haining Wang, Huajun Fang, and Litian Liu, "A Micromachined Piezoelectric Ultrasonic Transducer Operating in d33 Mode Using Square Interdigital Electrodes", IEEE SENSORS JOURNAL, Vol. 7, No. 7, pp. 967-976).

An ultrasound transducer described in Chao Wang, Zheyao Wang, Tian-Ling Ren, Senior Member, IEEE, Yiping Zhu, Yi Yang, Xiaoming Wu, Haining Wang, Huajun Fang, and Litian Liu, "A Micromachined Piezoelectric Ultrasonic Transducer Operating in d33 Mode Using Square Interdigital Electrodes", IEEE SENSORS JOURNAL, Vol. 7, No. 7, pp. 967-976 includes a lower electrode, a piezoelectric film laminated on the lower electrode, and an upper electrode laminated on the piezoelectric film. The ultrasound transducer described in Chao Wang, Zheyao Wang, Tian-Ling Ren, Senior Member, IEEE, Yiping Zhu, Yi Yang, Xiaoming Wu, Haining Wang, Huajun Fang, and Litian Liu, "A Micromachined Piezoelectric Ultrasonic Transducer Operating in d33 Mode Using Square Interdigital Electrodes", IEEE SENSORS JOURNAL, Vol. 7, No. 7, pp. 967-976 is known to have an area (effective area) which has a high contribution to piezoelectric change, and an area (reference area) which has a low contribution to piezoelectric change, in piezoelectric conversion.

However, a piezoelectric material used for ultrasound transducers, such as the ultrasound transducer described in Chao Wang, Zheyao Wang, Tian-Ling Ren, Senior Member, IEEE, Yiping Zhu, Yi Yang, Xiaoming Wu, Haining Wang, Huajun Fang, and Litian Liu, "A Micromachined Piezoelectric Ultrasonic Transducer Operating in d33 Mode Using Square Interdigital Electrodes", IEEE SENSORS JOURNAL, Vol. 7, No. 7, pp. 967-976 has a thin film having a thickness of not more than 10 μm, and it is hard to say that the thin film has a sufficient thickness relative to a grain size thereof. Therefore, it is difficult to keep piezoelectric characteristics constant by the grain size and distribution of the grains. In addition, it was difficult to keep an electrical characteristic constant between ultrasound transducers.

SUMMARY

A first object of the present invention is to provide an ultrasound probe capable of correcting variation in electrical characteristic between a plurality of ultrasound transducers on the basis of an output value from a reference area. A second object of the present invention is to provide a correction method for the ultrasound probe.

To achieve at least one of the abovementioned objects, according to an aspect of the present invention, an ultrasound probe reflecting one aspect of the present invention comprises: a plurality of ultrasound transducers each including a diaphragm, a lower electrode laminated on a surface of the diaphragm, a piezoelectric film laminated on a surface of the lower electrode, and including an effective area in which larger vibration is caused upon piezoelectric conversion, and a reference area in which smaller vibration than that in the effective area is caused upon piezoelectric conversion, and an upper electrode laminated on a surface of the piezoelectric film; and hardware processors that correct variation in performance between the ultrasound transducers, wherein one or both of the lower electrode and the upper electrode include an effective area electrode portion independently connected to the effective area, and a reference area electrode portion independently connected to the reference area, and each of the hardware processors is a device that corrects one or both of an output value from the effective area electrode portion and an input value to the effective area electrode portion on the basis of an output value from the reference area electrode portion.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, an ultrasound probe according to an embodiment of the present invention will be described with reference to the drawings. However, the scope of the invention is not limited to the disclosed embodiments.

[Configuration of Ultrasound Probe]

Figure 1A:
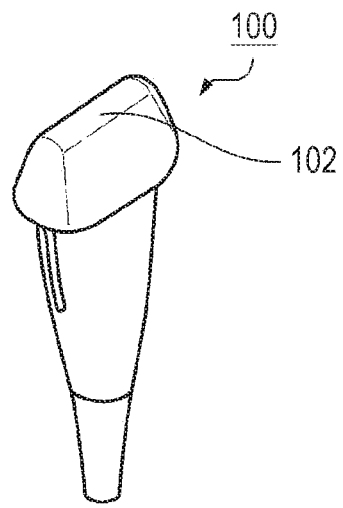
FIGS. 1A to 1C are diagrams illustrating configurations of an ultrasound probe according to an embodiment of the present invention.
Figure 1B:
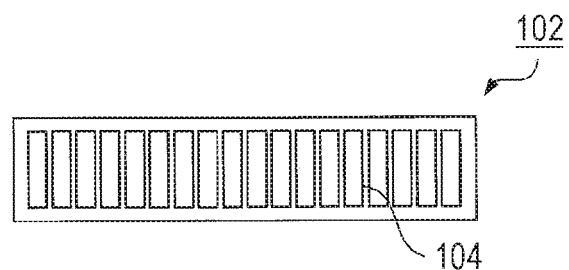
Figure 1C:
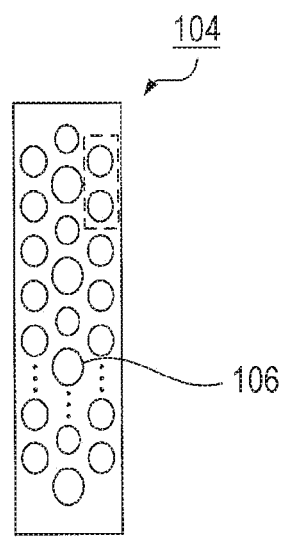
Figure 2:
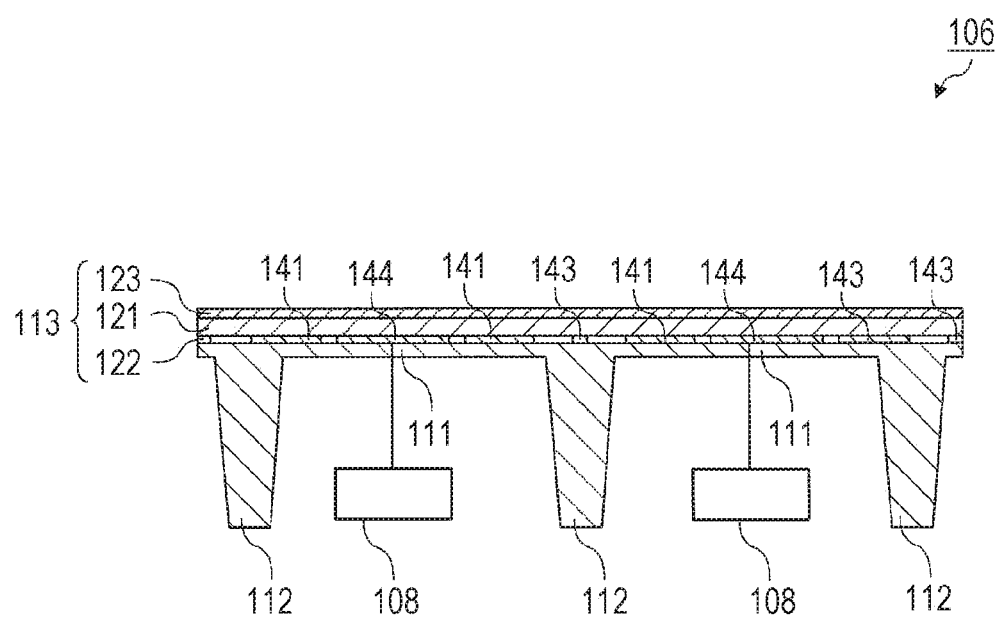
FIG. 2 is a cross-sectional view of ultrasound transducers.
Figure 3A:
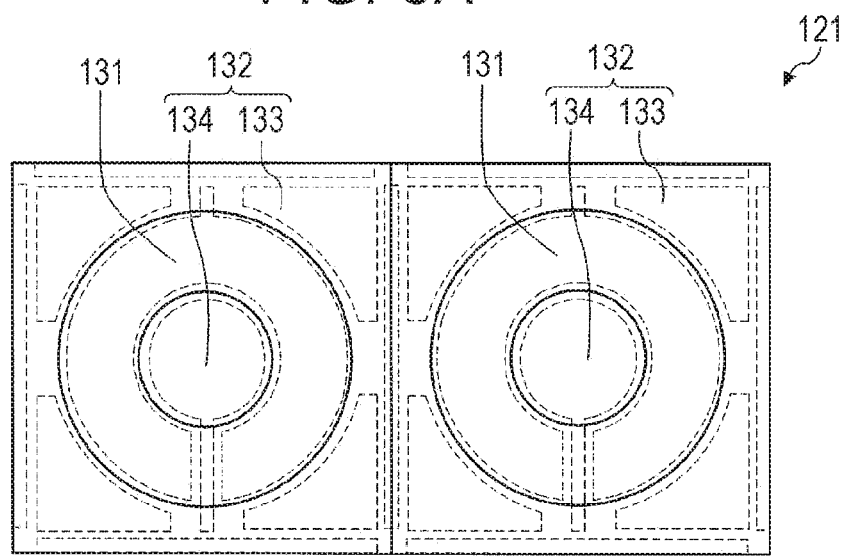
FIGS. 3A and 3B are plan views of a piezoelectric thin film and a lower electrode.
Figure 3B:
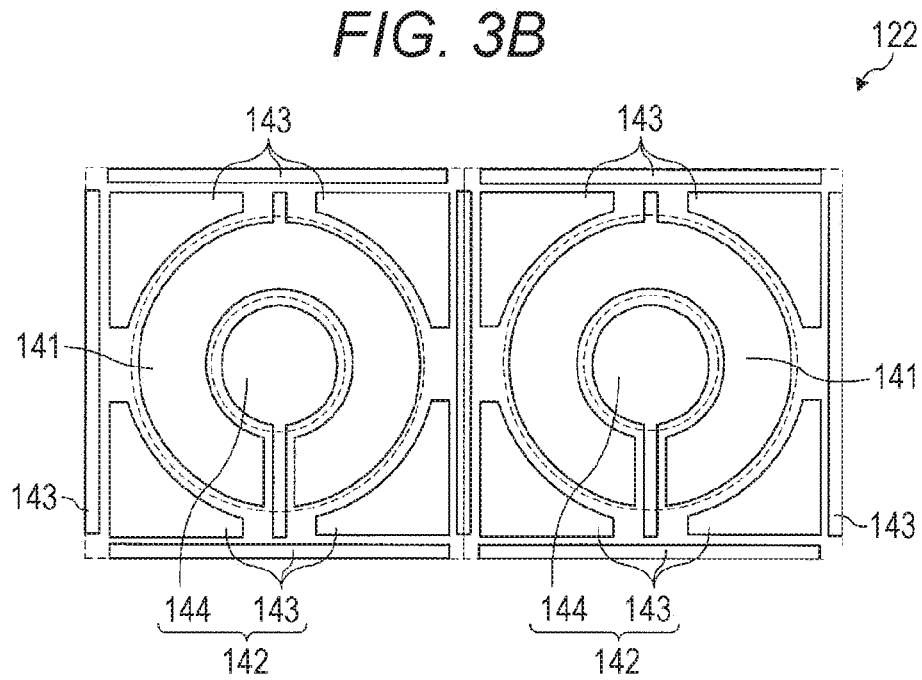

FIGS. 1A to 1C are diagrams illustrating configurations of an ultrasound probe. FIG. 1A is a schematic diagram illustrating a configuration of the ultrasound probe, FIG. 1B is a schematic diagram illustrating a configuration of a transducer unit, and FIG. 1C is a schematic diagram illustrating a configuration of ultrasound transducers. FIG. 2 is a cross-sectional view of an area indicated by a broken line in FIG. 1C. FIGS. 3A and 3B are plan views of a piezoelectric thin film and a lower electrode. FIG. 3A is a plan view of the piezoelectric thin film, and FIG. 3B is a plan view of the lower electrode.

As illustrated in FIG. 1A, the ultrasound probe 100 includes, for example, the transducer unit 102, a holder that holds the transducer unit 102, and correction units 108 (see FIG. 2) that correct variation in electrical characteristic between the ultrasound transducers. The holder includes, for example, an acoustic matching layer disposed on a surface of the transducer unit 102, and an acoustic lens disposed on a surface of the acoustic matching layer to be exposed from a surface (so as to constitute a surface) of the ultrasound probe 100.

As illustrated in FIG. 1B, in the transducer unit 102, transducer arrays 104 are disposed in parallel. As illustrated in FIG. 1C, in each of the transducer arrays 104, the ultrasound transducers 106 are disposed in parallel. In the present embodiment, 45,696 ultrasound transducers 106 are arranged in parallel.

As illustrated in FIG. 2, each of the ultrasound transducers 106 includes a diaphragm portion 111, support portions 112 that support the periphery of the diaphragm portion 111, and a piezoelectric element portion 113 disposed on the diaphragm portion 111. The diaphragm portion 111 and the support portions 112 are made of, for example, silicon. In the present embodiment, the diaphragm portion 111 and the support portions 112 are integrally formed.

The piezoelectric element portion 113 includes a piezoelectric film 121, and the lower electrode 122 and an upper electrode 123 disposed to hold the piezoelectric film 121 from the front and back sides. In the piezoelectric element portion 113, the lower electrode 122 is laminated on a surface of the diaphragm portion 111, the piezoelectric film 121 is laminated on a surface of the lower electrode 122, and the upper electrode 123 is laminated on a surface of the piezoelectric film 121.

The piezoelectric film 121 is, for example, a piezoelectric thin film having a perovskite structure containing lead, more specifically, so-called lead zirconate titanate (PZT). The piezoelectric film 121 preferably has a thickness not more than ¼ of acoustic wavelength, more preferably not more than $\frac{1}{10}$ thereof, for example, within the range of 0.1 to 10 µm. In MEMS using a thin film as in the present embodiment, "flexural vibration" is used to cause bending a piezoelectric film locally reduced in thickness. Therefore, the piezoelectric film has a flexible area and an inflexible area, and the inflexible area can be used for the correction method for the ultrasound probe 100.

As illustrated in FIGS. 2 and 3A, the piezoelectric film 121 has an effective area 131 and a reference area 132. Here, the "effective area 131" means an area in which larger vibration is caused upon piezoelectric conversion. In addition, the "reference area 132" means an area in which smaller vibration than that in the effective area 131 is caused upon piezoelectric conversion. The effective area 131 and the reference area 132 are areas determined relatively as a result of comparing the magnitudes of vibration upon piezoelectric conversion, and cannot be uniquely determined. Therefore, the effective area 131 and the reference area 132 are different between ultrasound transducers 106. The reference area 132 includes a first reference area 133 corresponding to the support portions 112, and a second reference area 134 other than the first reference area 133.

In the present embodiment, a central portion of the piezoelectric film 121 and an outer peripheral portion of the piezoelectric film 121 are the reference area 132. That is, the central portion of the piezoelectric film 121 is the second reference area 134, and the outer peripheral portion of the piezoelectric film 121 is the first reference area 133. Furthermore, an annular area between the central portion of the piezoelectric film 121 and the outer peripheral portion of the piezoelectric film 121 is the effective area 131.

As illustrated in FIGS. 2 and 3B, the lower electrode 122 is laminated on the surface of the diaphragm portion 111, and a piezoelectric film 121 is laminated on a surface of the lower electrode 122 opposite to the diaphragm portion 111. The lower electrode 122 has, for example, a thin layer of gold. The lower electrode 122 has a thickness of 50 to 500 nm, preferably 100 to 200 nm.

The lower electrode 122 includes an effective area electrode portion 141 and a reference area electrode portion 142. The effective area electrode portion 141 and the reference area electrode portion 142 are separated so that the effective area electrode portion 141 and the reference area electrode portion 142 are electrically independent of each other. For example, the effective area electrode portion 141 and the reference area electrode portion 142 are separated from each other across a space so that the effective area electrode portion 141 and the reference area electrode portion 142 are not electrically connected to each other.

The effective area electrode portion 141 is disposed corresponding to the effective area 131 of the piezoelectric film 121, and is independently connected to the effective area 131 from the back side. In the present embodiment, the effective area electrode portion 141 is formed in a substantially annular shape, corresponding to the effective area 131. Note that the effective area electrode portion 141 is preferably disposed on the entire effective area 131, and may be divided into a plurality of areas.

The reference area electrode portion 142 is disposed corresponding to the reference area 132 of the piezoelectric film 121, and is independently connected to the reference area 132 from the back side. In the present embodiment, the reference area electrode portion 142 includes a first reference area electrode portion 143 connected to the first reference area 133, and a second reference area electrode portion 144 connected to the second reference area 134.

The upper electrode 123 is laminated on a surface of the piezoelectric film 121 opposite to a surface on which the lower electrode 122 is disposed. The upper electrode has, for example, a thin layer of gold. The upper electrode 123 has a thickness of 50 to 500 nm, preferably 100 to 200 nm.

Each of The correction units 108 is a device for correcting one or both of an output value from the effective area electrode portion 141 and an input value to the effective area electrode portion 141, on the basis of an output value from the reference area electrode portion 142. These output and input values are, for example, voltage values. The correction units 108 have a CPU or the like including, for example, a storage unit and a calculation unit to perform various arithmetic processing or the like as described below.

When the reference area 132 has an electrical characteristic being "electric charges remaining in the reference area 132 after polarization", first of all, the correction units 108 each detect an output value from the reference area electrode portion 142. Then, the correction units 108 each determine an amount of electric charges remaining in the reference area 132 after polarization determine a polarization amount in the effective area, and correct one or both of a voltage value from the effective area electrode portion 141 and an input value to the effective area electrode portion 141 to compensate for variation in polarization amount between the effective areas 131.

When the reference area 132 has an electrical characteristic being "electric charges due to electrostatic induction in the reference area 132", first of all, the correction units 108 each detect an output value from the reference area electrode portion 142 including electric charges due to electrostatic induction in the reference area 132. Then, the correction units 108 each determine the amount of electric charges due to electrostatic induction in the reference area 132, determine the amount of electric charges due to electrostatic induction between the effective areas 131, and correct one or both of a voltage value from the effective area electrode portion 141 and an input value to the effective area electrode portion 141 to cancel electrostatic induction between the effective areas 131.

When the reference area 132 has an electrical characteristic being "electric charges due to temperature of the reference area 132 according to temperature distribution between the reference areas 132", the correction units 108 each detect an output value from the reference area electrode portion 142 including electric charges due to temperature of the reference area 132 according to temperature distribution between the reference areas 132. Then, the correction units 108 each determine the amount of electric charges due to temperature of the reference area 132, determines variation in amount of electric charges due to temperature distribution between the effective areas 131, and correct one or both of an output value from the effective area 131 and an input value to the effective area electrode portion 141 to compensate for variation in temperature between the effective areas 131.

When the reference area 132 has an electrical characteristic being "electric charges due to reception of an acoustic signal in the reference area 132", the correction units 108 each detect an output value from the reference area electrode portion 142 including electric charges due to reception of an acoustic signal in the reference area 132. Then, the correction units 108 each determine the amount of electric charges due to reception of an acoustic signal in the reference area 132, determine variation in amount of electric charges due to an acoustic signal between the effective areas 131, and correct one or both of an output value from the effective area 131 and an input value to the effective area electrode portion 141 to compensate for variation in acoustic signal between the effective areas 131.

Each of the support portions 112 is formed integrally with the diaphragm portion 111. The shape of the support portion 112 is not particularly limited, as long as the support portion 112 can support the ultrasound transducer 106. In the present embodiment, the support portion 112 has a cylindrical shape or a non-cylindrical shape such as an elliptical shape. The cylinder has an upper surface on which each ultrasound transducer 106 is supported.

The acoustic matching layer is a layer for matching an acoustic characteristic between the piezoelectric element portion 113 and the acoustic lens. The acoustic matching layer has a single layer structure or a laminated structure made of a resin such as epoxy resin or silicone resin, or an inorganic material such as aluminum or an alloy thereof. The acoustic lens includes a flexible material having an acoustic impedance between a subject and the acoustic matching layer. The material is, for example, a silicone-based rubber, such as silicone rubber or fluorine silicone rubber. For disposition of the acoustic matching layer and the acoustic lens, an adhesive (e.g., epoxy-based adhesive or silicone-based adhesive) normally used in the technical field is used as necessary.

[Correction Method for Ultrasound Probe]

Next, a correction method for the ultrasound probe 100 will be described. The correction method for the ultrasound probe 100 includes a first step of detecting an output value in which an electrical characteristic of the reference area 132 is reflected, from the reference area electrode portion 142, and a second step of correcting, on the basis of the electrical characteristic, one or both of an output value from the effective area electrode portion 141 and an input value to the effective area electrode portion 141 to compensate for variation in piezoelectric characteristic between the effective areas 131. Here, the "electrical characteristic of the reference area 132" includes (1) electric charges remaining in the reference area 132 after polarization, (2) electric charges due to electrostatic induction in the reference area 132, (3) electric charges due to temperature of the reference area 132 according to temperature distribution between the reference areas 132, (4) electric charges due to reception of an acoustic signal in the reference area 132, or the like. A correction method for the ultrasound probe 100 in each electrical characteristic will be described below. These correction methods for the ultrasound probes 100 is a method of correcting the ultrasound probe 100 as a whole by correcting each ultrasound transducer 106.

(Correction Method for Ultrasound Probe 1)

The correction method for the ultrasound probe 100 where the electrical characteristic of the reference area 132 is "electric charges remaining in the reference area 132 after polarization" will be described.

The first step of the correction method for the ultrasound probe 100 where the electrical characteristic of the reference area 132 is "electric charges remaining in the reference area 132 after polarization" is a step of detecting an output value from the reference area electrode portion 142. Furthermore, the second step includes the steps of determining an amount of electric charges remaining in the reference area 132 after polarization, determining a polarization amount in the effective area, and correcting one or both of a voltage value from the effective area electrode portion 141 and an input value to the effective area electrode portion 141 to compensate for variation in polarization amount between the effective areas 131.

In the first step, an output value from the reference area electrode portion 142 is detected. It is known that electric charges remain in the reference area 132 for a certain period after polarization. Therefore, in the first step, an output value from the reference area electrode portion 142 is detected, including electric charges remaining in the reference area 132 after polarization.

In the second step, in the step of determining an amount of electric charges in the reference area 132, an amount of electric charges in the reference area 132 is determined on the basis of the output value (voltage value) from the reference area electrode portion 142. Specifically, the amount of electric charges in the reference area 132 is determined as an amount of electric charges with respect to the voltage value from the reference area electrode portion 142, on the basis of a relationship between the amount of electric charges and the voltage value, which is previously determined.

In the second step, in the step of determining a polarization amount in the effective area, a polarization amount in the effective area 131 is determined on the basis of the amount of electric charges in the reference area 132. Specifically, the amount of electric charges in the effective area 131 is estimated on the basis of the amount of electric charges in the reference area 132, using the proximity between the reference area 132 and the effective area 131. Then, the polarization amount which would have remained in the effective area 131 is determined on the basis of the amount of electric charges in the effective area 131. Specifically, the polarization amount in the effective area 131 is determined as a polarization amount with respect to the amount of electric charges in the effective area 131, on the basis of a relationship between the amount of electric charges in the effective area 131 and the polarization amount in the effective area 131 determined in advance.

In the step of correction in the second step, one or both of a voltage value from the effective area electrode portion 141 and an input value to the effective area electrode portion 141 are corrected to compensate for variation in polarization amount between the effective areas 131. Specifically, in order to eliminate variation between a polarization amount in an effective area 131 to be corrected and a polarization amount in the other effective area 131, correction is made on one or both of a voltage value from the corresponding effective area electrode portion 141 and an input value to the effective area electrode portion 141. That is, only an output value from the effective area electrode portion 141 may be corrected to eliminate variation in polarization amount between the effective areas 131, only an input value to the effective area electrode portion 141 may be corrected to eliminate variation in polarization amount between the effective areas 131, or only an output value from the effective area electrode portion 141 and an input value to the effective area electrode portion 141 may be corrected to eliminate variation in polarization amount between the effective areas 131.

Since the polarization is performed uniformly over the entire piezoelectric film 121, polarization amounts remaining in the first reference area 133 and the second reference area 134 are considered to be substantially the same. Therefore, in the first step, an output value from the first reference area electrode portion 143 is preferably detected, including electric charges remaining in the first reference area 133 after polarization, or an output value from the second reference area electrode portion 144 is preferably detected, including electric charges remaining in the second reference area 134 after polarization. In addition, in the first step, an output value from the first reference area electrode portion 143 may be detected, including electric charges remaining in the first reference area 133 after polarization, and an output value from the second reference area electrode portion 144 may be detected, including electric charges remaining in the second reference area 134 after polarization. In this configuration, an average value of the output value from the first reference area electrode portion 143, and the output value from the second reference area electrode portion 144 is defined as the output value from the reference area electrode portion 142.

(Correction Method for Ultrasound Probe 2)

The first step of the correction method for the ultrasound probe 100 where the electrical characteristic of the reference area 132 is "electric charges due to electrostatic induction in the reference area 132" is a step of detecting an output value from the reference area electrode portion 142 including electric charges due to electrostatic induction in the reference area 132. Furthermore, the second step includes the steps of determining an amount of electric charges due to electrostatic induction in the reference area 132, determining an amount of electric charges due to electrostatic induction between the effective areas 131, and correcting one or both of a voltage value from the effective area electrode portion 141 and an input value to the effective area electrode portion 141 to cancel electrostatic induction between the effective areas 131.

In the first step, an output value from the reference area electrode portion 142 is detected. In the ultrasound probe 100, the piezoelectric film 121 sometimes vibrates largely due to electrostatic induction. Therefore, in the first step, an output value from the reference area electrode portion 142 is detected, including electric charges generated in the reference area 132 by electrostatic induction. Note that in the first step, it is preferable to detect an output value from the first reference area electrode portion 143.

In the second step, in the step of determining an amount of electric charges in the reference area, an amount of electric charges due to electrostatic induction in the reference area 132 is determined on the basis of the output value (voltage value) from the reference area electrode portion 142. Specifically, the amount of electric charges due to electrostatic induction in the reference area 132 is determined as an amount of electric charges with respect to the voltage value from the reference area electrode portion 142, on the basis of a relationship between the amount of electric charges due to electrostatic induction and the voltage value, which is previously determined.

In the second step, in the step of determining an amount of electric charges between the effective areas 131, an amount of electric charges between the effective areas is determined on the basis of the amount of electric charges in the reference area 132.

In the step of correction in the second step, one or both of a voltage value from the effective area electrode portion 141 and an input value to the effective area electrode portion 141 are corrected to cancel electrostatic induction between the effective areas 131. Specifically, in order to eliminate variation between electrostatic induction in an effective area 131 to be corrected and electrostatic induction in the other effective area 131, correction is made on one or both of a voltage value from the corresponding effective area electrode portion 141 and an input value to the effective area electrode portion 141. That is, only an output value from the effective area electrode portion 141 may be corrected to eliminate variation in electrostatic induction between the effective areas 131, only an input value to the effective area electrode portion 141 may be corrected to eliminate variation in electrostatic induction between the effective areas 131, or both of a voltage value from the effective area electrode portion 141 and an input value to the effective area electrode portion 141 may be corrected to eliminate variation in electrostatic induction between the effective areas 131.

(Correction Method for Ultrasound Probe 3)

The first step of the correction method for the ultrasound probe 100 where the electrical characteristic of the reference area 132 is "electric charges due to temperature of the reference area 132 according to temperature distribution between the reference areas 132" is a step of detecting an output value from the reference area electrode portion 142 including electric charges due to temperature of the reference area 132 according to temperature distribution between the reference areas 132. Furthermore, the second step includes the steps of determining an amount of electric charges due to temperature of the reference area 132, determining variation in amount of electric charges due to temperature distribution between the effective areas 131, and correcting one or both of an output value from the effective area 131 and an input value to the effective area electrode portion 141 to compensate for variation in temperature between the effective areas 131.

In the first step, an output value from the reference area electrode portion 142 is detected. In the ultrasound probe 100, a detection value detected from the reference area electrode portion 142 may differ depending on the temperature. Therefore, in the first step, an output value from the reference area electrode portion 142 is detected, including the electric charges due to temperature of the reference area 132 according to temperature distribution between the reference areas 132. Since the first reference area 133 is in contact with the support portion 112, the temperature of the first reference area 133 may be affected by the support portion 112. Therefore, in the first step, an output value is preferably detected from the second reference area electrode portion 144.

In the second step, in the step of obtaining an amount of electric charges due to temperature of the reference area 132, an amount of electric charges due to temperature of the reference area 132 is determined on the basis of the output value (voltage value) from the reference area electrode portion 142. Specifically, the amount of electric charges due to temperature of the reference area 132 is determined as an amount of electric charges with respect to the voltage value from the reference area electrode portion 142, on the basis of a relationship between the amount of electric charges due to temperature and the voltage value, which is previously determined.

In the second step, in the step of determining an amount of electric charges between the effective areas 131, an amount of electric charges between the effective areas 131 is determined on the basis of the amount of electric charges in the reference area 132.

In the step of correction in the second step, one or both of an output value from the effective area 131 and an input value to the effective area electrode portion 141 are corrected to compensate for variation in amount of electric charges between the effective areas 131. Specifically, in order to eliminate variation between an amount of electric charges at the temperature of an effective area 131 to be corrected and an amount of electric charges at the temperature of another effective area 131, correction is made on one or both of a voltage value from the corresponding effective area electrode portion 141 and an input value to the effective area electrode portion 141. That is, only an output value from the effective area electrode portion 141 may be corrected to eliminate variation in amount of electric charges at temperature between the effective areas 131, only an input value to the effective area electrode portion 141 may be corrected to eliminate variation in amount of electric charges at temperature between the effective areas 131, or both of a voltage value from the effective area electrode portion 141 and an input value to the effective area electrode portion 141 may be corrected to eliminate variation in amount of electric charges at temperature between the effective areas 131.

(Correction Method for Ultrasound Probe 4)

The first step of the correction method for the ultrasound probe 100 where the electrical characteristic of the reference area 132 is "electric charges due to reception of an acoustic signal in the reference area 132" is a step of detecting an output value from the reference area electrode portion 142 including electric charges due to reception of an acoustic signal in the reference area 132. Furthermore, the second step includes the steps of determining an amount of electric charges due to reception of an acoustic signal in the reference area 132, determining variation in amount of electric charges due to an acoustic signal between the effective areas 131, and correcting one or both of an output value from the effective area 131 and an input value to the effective area electrode portion 141 to compensate for variation in acoustic signal between the effective areas 131.

In the first step, an output value from the reference area electrode portion 142 is detected. In the transducer unit 102 according to the present embodiment, the reference area 132 has low response to an acoustic signal, and the effective area has high response to an acoustic signal. Therefore, in the first step, an output value from the first reference area electrode portion 143 is preferably detected, including electric charges due to reception of an acoustic signal in the reference area 132.

In the second step, in the step of obtaining an amount of electric charges in the reference area, an amount of electric charges due to reception of an acoustic signal in the reference area 132 is determined on the basis of the output value (voltage value) from the reference area electrode portion 142. Specifically, the amount of electric charges due to reception of an acoustic signal in the reference area 132 is determined as an amount of electric charges with respect to the voltage value from the reference area electrode portion 142, on the basis of a relationship between the amount of electric charges due to reception of an acoustic signal and the voltage value, which is previously determined.

In the second step, in the step of determining an amount of electric charges between the effective areas 131, variation in amount of electric charges due to an acoustic signal between the effective areas is determined on the basis of the amount of electric charges in the reference area 132.

In the step of correction in the second step, one or both of a voltage value from the effective area electrode portion 141 and an input value to the effective area electrode portion 141 are corrected to compensate for variation in acoustic signal between the effective areas 131. Specifically, in order to eliminate variation between an acoustic signal in an effective area 131 to be corrected and an acoustic signal in the other effective area 131, correction is made on one or both of a voltage value from the corresponding effective area electrode portion 141 and an input value to the effective area electrode portion 141. That is, only an output value from the effective area electrode portion 141 may be corrected to eliminate variation in acoustic signal between the effective areas 131, only an input value to the effective area electrode portion 141 may be corrected to eliminate variation in acoustic signal between the effective areas 131, or both of a voltage value from the effective area electrode portion 141 and an input value to the effective area electrode portion 141 may be corrected to eliminate variation in acoustic signal between the effective areas 131.

As described above, in the correction method for the ultrasound probe 100 according to the present invention, one or both of an output value from the effective area electrode portion 141 and an input value to the effective area electrode portion 141 are corrected, on the basis of an output value taking account of an electrical characteristic of the reference area 132 to compensate for variation in any of piezoelectric characteristics of (1) to (4) between the effective areas 131, as described above. Thus, the ultrasound probe 100 can provide a constant output value (voltage value) therefrom. In addition, since correction information (voltage value) can be obtained from the piezoelectric film 121 for piezoelectric conversion, correction can be appropriately performed even if the ultrasound probe 100 is deteriorated.

[Configuration of Ultrasound Imaging Apparatus]

Figure 4A:
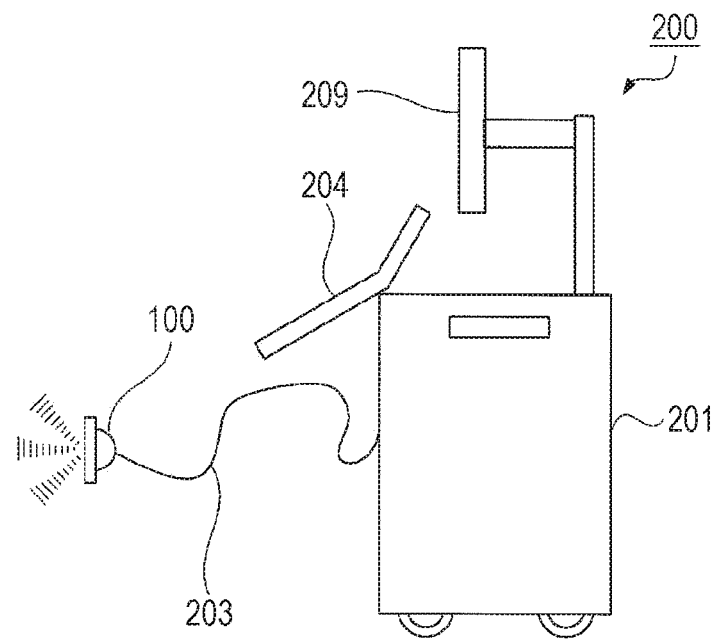
FIGS. 4A and 4B are diagrams illustrating configurations of an ultrasound imaging apparatus according to an embodiment of the present invention.
Figure 4B:
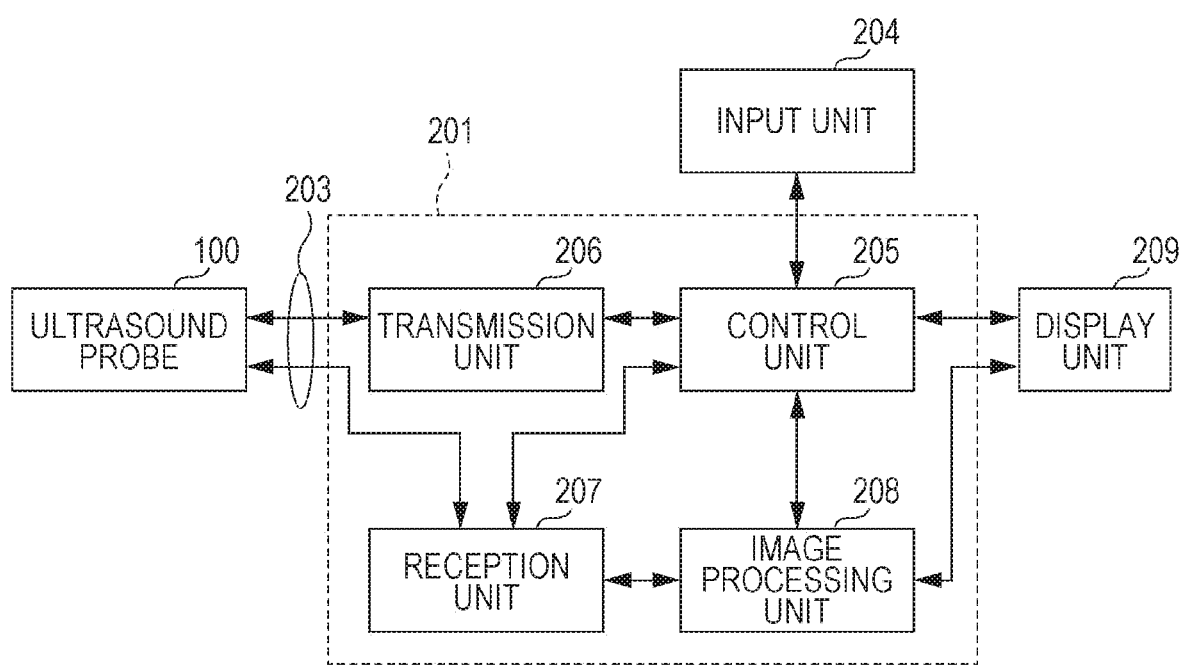

Next, a configuration of an ultrasound imaging apparatus 200 having the ultrasound probe 100 described above will be described. As long as the ultrasound imaging apparatus 200 has the ultrasound probe 100 described above, the ultrasound imaging apparatus 200 is not particularly limited in configuration, and may adopt a known configuration. FIGS. 4A and 4B are diagrams illustrating configurations of the ultrasound imaging apparatus. FIG. 4A is a schematic diagram illustrating a configuration of the ultrasound imaging apparatus, and FIG. 4B is a block diagram illustrating an electrical configuration of the ultrasound imaging apparatus.

As illustrated in FIGS. 4A and 4B, the ultrasound imaging apparatus 200 includes an apparatus body 201, an ultrasound probe 100 connected to the apparatus body 201 through a cable 203, and an input unit 204 and a display unit 209 disposed on the apparatus body 201

The apparatus body 201 includes a control unit 205 connected to the input unit 204, a transmission unit 206 and a reception unit 207 connected to the control unit 205 and the cable 203, and an image processing unit 208 connected to the reception unit 207 and the control unit 205. Note that the control unit 205 and the image processing unit 208 are each connected to the display unit 209.

The input unit 204 is, for example, a device for input of a command for instructing the start of diagnosis or the like, or data such as personal information of a subject. The configuration of the input unit 204 is not particularly limited, as long as the input unit 204 can exhibit the above function. The input unit 204 includes, for example, an operation panel including a plurality of input switches, a keyboard, or the like.

The control unit 205 is a circuit that wholly controls the ultrasound imaging apparatus 200. The control unit 205 controls the ultrasound probe 100, the input unit 204, the transmission unit 206, the reception unit 207, the image processing unit 208, and the display unit 209 according to their respective functions. The control unit 205 has, for example, a microprocessor and a memory element, and their peripheral circuits.

The transmission unit 206 transmits, for example, a signal from the control unit 205 to the ultrasound probe 100. Specifically, the transmission unit 206 is a circuit that supplies a driving signal as an electric signal to the ultrasound probe 100 through the cable 203, under the control of the control unit 205, and causes the ultrasound probe 100 to generate an ultrasonic wave to be transmitted. The reception unit 207 receives, for example, a signal from the ultrasound probe 100, and outputs the signal to the control unit 205 or the image processing unit 208. Specifically, the reception unit 207 is a circuit that receives a reception signal being an electric signal from the ultrasound probe 100 through the cable 203, under the control of the control unit 205.

For example, the image processing unit 208 is a circuit that forms an image (ultrasound image) representing an internal state in the subject on the basis of the signal received by the reception unit 207, under the control of the control unit 205. For example, the image processing unit 208 includes a digital signal processor (DSP) that generates an ultrasound image of the subject, a digital-analog conversion circuit (DAC circuit) that converts a signal processed by the DSP, from a digital signal to an analog signal, and the like.

The display unit 209 is, for example, a device that displays an ultrasound image of the subject generated by the image processing unit 208, under the control of the control unit 205. The display unit 209 includes, for example, a display device such as a CRT display, a liquid crystal display (LCD), an organic EL display, or a plasma display, or a printing device such as a printer.

In the present embodiment, the lower electrode 122 constitutes the effective area electrode portion 141 and the reference area electrode portion 142, but the upper electrode 123 may constitute the effective area electrode portion 141 and the reference area electrode portion 142, or the lower electrode 122 and the upper electrode 123 may constitute the effective area electrode portion 141 and the reference area electrode portion 142. When the upper electrode 123 constitutes the effective area electrode portion 141 and the reference area electrode portion 142, the upper electrode 123 includes the effective area electrode portion 141 independently connected to the effective area 131 from the surface side, and the reference area electrode portion 142 independently connected to the reference area 132 from the surface side. Furthermore, when the lower electrode 122 and the upper electrode 123 constitute the effective area electrode portion 141 and the reference area electrode portion 142, the upper electrode 123 includes the effective area electrode portion 141 independently connected to the effective area 131 from the surface side, and the reference area electrode portion 142 independently connected to the reference area 132 from the surface side. Furthermore, the lower electrode 122 includes the effective area electrode portion 141 independently connected to the effective area 131 from the back side, and the reference area electrode portion 142 independently connected to the reference area 132 from the back side. Furthermore, the upper electrode 123 may include the effective area electrode portion 141, and the lower electrode 122 may include the reference area electrode portion 142. Furthermore, the upper electrode 123 may include the reference area electrode portion 142, and the lower electrode 122 may include the effective area electrode portion 141.

Note that in the present embodiment, the correction units 108 are included in the ultrasound probe 100, but the correction units 108 may be positioned outside the ultrasound probe 100, for example, in the control unit 205 of the ultrasound imaging apparatus 200. Furthermore, the correction units 108 may be configured to be connected to the ultrasound imaging apparatus 200 from outside.

The ultrasound probe according to the present invention can provide an ultrasound probe having an ultrasound transducer having a constant electrical characteristic. Therefore, according to the correction method described above, the ultrasound probe is expected to have further improved performance and to be widely used.

Although embodiments of the present invention have been described and illustrated in detail, it is clearly understood that the same is by way of illustration and example only and not limitation, the scope of the present invention should be interpreted by terms of the appended claims.

What is claimed is:

1. An ultrasound probe comprising:
    a plurality of ultrasound transducers each including a diaphragm, a lower electrode laminated on a surface of the diaphragm, a piezoelectric film laminated on a surface of the lower electrode, and including an effective area in which larger vibration is caused upon piezoelectric conversion, and a reference area in which smaller vibration than that in the effective area is caused upon piezoelectric conversion, and an upper electrode laminated on a surface of the piezoelectric film; and
    hardware processors that correct variation in performance between the ultrasound transducers, wherein, in each of the plurality of ultrasound transducers, one or both of the lower electrode and the upper electrode include an effective area electrode portion independently connected to the effective area, and a reference area electrode portion independently connected to the reference area, and each of the hardware processors is a device that corrects, in a respective one of the transducers, one or both of an output value from the effective area electrode portion and an input value to the effective area electrode portion on the basis of an output value from the reference area electrode portion.

2. The ultrasound probe according to claim 1, wherein the each of the hardware processors is a device that, for the respective one of the transducers, after detection of the output value from the reference area electrode portion including electric charges remaining in the reference area after polarization, determines an amount of electric charges remaining in the reference area after polarization, determines a polarization amount in the effective area on the basis of the amount of electric charges, and corrects one or both of a voltage value from the effective area electrode portion and an input value to the effective area electrode portion to compensate for variation in polarization amount between the effective areas.

3. The ultrasound probe according to claim 2, wherein the reference area of the each of the plurality of ultrasound transducers includes a first reference area corresponding to a support portion that supports each of the ultrasound transducers, and a second reference area other than the first reference area, the reference area electrode portion of the each of the plurality of ultrasound transducers includes one or both of a first reference area electrode portion connected to the first reference area and a second reference area electrode portion connected to the second reference area, and the each of the hardware processors performs, for the respective one of the transducers, one or both of detection of an output value from the first reference area electrode portion including electric charges remaining in the first reference area after polarization, and detection of an output value from the second reference area electrode portion including electric charges remaining in the second reference area after polarization.

4. The ultrasound probe according to claim 1, wherein the each of the hardware processors is a device that, for the respective one of the transducers, after detection of the output value from the reference area electrode portion including electric charges due to electrostatic induction in the reference area, determines an amount of electric charges due to electrostatic induction in the reference area, determines an amount of electric charges due to electrostatic induction between the effective areas on the basis of the amount of electric charges, and corrects one or both of an output value from the effective area electrode portion and an input value to the effective area electrode portion to compensate for variation in electrostatic induction between the effective areas.

5. The ultrasound probe according to claim 4, wherein, in the each of the plurality of ultrasound transducers, the reference area is a first reference area corresponding to the area of a support portion that supports each of the ultrasound transducers, and the reference area electrode portion is a first reference area electrode portion connected to the first reference area.

6. The ultrasound probe according to claim 1, wherein the each of the hardware processors is a device that, for the respective one of the transducers, after detection of the output value from the reference area electrode portion including electric charges due to temperature of the reference area according to temperature distribution between the reference areas, determines an amount of electric charges due to temperature of the reference area, determines variation in amount of electric charges due to temperature distribution between the effective areas, on the basis of the amount of electric charges, and corrects one or both of an output value from the effective area and an input value to the effective area electrode portion to compensate for variation in temperature between the effective areas.

7. The ultrasound probe according to claim 6, wherein, in the each of the plurality of ultrasound transducers, the reference area includes a first reference area corresponding to the area of a support portion that supports each of the ultrasound transducers, and a second reference area other than the first reference area, and the reference area electrode portion is a second reference area electrode portion connected to the second reference area.

8. The ultrasound probe according to claim 1, wherein the each of the hardware processors is a device that, for the respective one of the ultrasound transducers, after detection of an output value from the reference area electrode portion including electric charges due to reception of an acoustic signal in the reference area, determines an amount of electric charges due to reception of an acoustic signal in the reference area, determines variation in amount of electric charges due to an acoustic signal between the effective areas on the basis of the amount of electric charges, and corrects one or both of an output value from the effective area electrode portion and an input value to the effective area electrode portion to compensate for variation in acoustic signal between the effective areas.

9. The ultrasound probe according to claim 8, wherein, in the each of the plurality of ultrasound transducers, the reference area includes a first reference area corresponding to the area of a support portion that supports each of the ultrasound transducers, and the reference area electrode portion is a first reference area electrode portion connected to the first reference area.

10. A correction method for an ultrasound probe including a plurality of ultrasound transducers each including:

a diaphragm;

a lower electrode disposed on the diaphragm;

a piezoelectric film disposed on the lower electrode; and an upper electrode disposed on the piezoelectric film, the piezoelectric film including an effective area in which larger vibration is caused upon piezoelectric conversion, and a reference area in which smaller vibration than that in the effective area is caused upon piezoelectric conversion, one or both of the lower electrode and the upper electrode including an effective area electrode portion independently connected to the effective area, and a reference area electrode portion independently connected to the reference area, the method comprising:

detecting, in the each of the plurality of ultrasound transducers, an output value in which an electrical characteristic of the reference area is reflected, from the reference area electrode portion; and correcting, in the each of the plurality of ultrasound transducers, one or both of an output value from the effective area electrode portion and an input value to the effective area electrode portion to compensate for variation in piezoelectric characteristic between the effective areas, on the basis of the electrical characteristic.

11. The correction method for an ultrasound probe according to claim 10, wherein the detecting includes detecting an output value from the reference area electrode portion including electric charges remaining in the reference area after polarization, and the correcting includes:

determining an amount of electric charges remaining in the reference area after polarization;

determining a polarization amount in the effective area on the basis of the amount of electric charges; and correcting one or both of a voltage value from the effective area electrode portion and an input value to the effective area electrode portion to compensate for variation in polarization amount between the effective areas.

12. The correction method for an ultrasound probe according to claim 11, wherein the reference area includes a first reference area corresponding to a support portion that supports the each of the plurality of ultrasound transducers, and a second reference area other than the first reference area, the reference area electrode portion includes one or both of a first reference area electrode portion connected to the first reference area and a second reference area electrode portion connected to the second reference area, and the detecting includes one or both of detecting an output value from the first reference area electrode portion including electric charges remaining in the first reference area after polarization, and detecting an output value from the second reference area electrode portion including electric charges remaining in the second reference area after polarization.

13. The correction method for an ultrasound probe according to claim 10, wherein the detecting includes detecting an output value from the reference area electrode portion including electric charges due to electrostatic induction in the reference area, the correcting includes:

determining an amount of electric charges due to electrostatic induction in the reference area;

determining an amount of electric charges due to electrostatic induction between the effective areas on the basis of the amount of electric charges; and correcting one or both of an output value from the effective area electrode portion and an input value to the effective area electrode portion to compensate for variation in electrostatic induction between the effective areas.

14. The correction method for an ultrasound probe according to claim 13, wherein the reference area is a first reference area corresponding to the area of a support portion that supports the each of the plurality of ultrasound transducers, and the reference area electrode portion is a first reference area electrode portion connected to the first reference area.

15. The correction method for an ultrasound probe according to claim 10, wherein the detecting includes detecting an output value from the reference area electrode portion including electric charges due to temperature of the reference area according to temperature distribution between the reference areas, the correcting includes:

determining an amount of electric charges due to temperature of the reference area;

determining variation in amount of electric charges due to temperature distribution between the effective areas, on the basis of the amount of electric charges; and correcting one or both of an output value from the effective area and an input value to the effective area electrode portion to compensate for variation in temperature between the effective areas.

16. The correction method for an ultrasound probe according to claim 15, wherein the reference area includes a first reference area corresponding to the area of a support portion that supports each of the ultrasound transducers, and a second reference area other than the first reference area, and the reference area electrode portion is a second reference area electrode portion connected to the second reference area.

17. The correction method for an ultrasound probe according to claim 10, wherein the detecting includes detecting an output value from the reference area electrode portion including electric charges due to reception of an acoustic signal in the reference area, the correcting includes:

determining an amount of electric charges due to reception of an acoustic signal in the reference area;

determining variation in amount of electric charges due to an acoustic signal between the effective areas on the basis of the amount of electric charges; and correcting one or both of an output value from the effective area electrode portion and an input value to the effective area electrode portion to compensate for variation in acoustic signal between the effective areas.

18. The correction method for an ultrasound probe according to claim 17, wherein the reference area includes a first reference area corresponding to the area of a support portion that supports the each of the plurality of ultrasound transducers, and the reference area electrode portion is a first reference area electrode portion connected to the first reference area.

* * * * *